United States Patent
Lyu et al.

(10) Patent No.: US 12,193,803 B2
(45) Date of Patent: Jan. 14, 2025

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventors: Jingyuan Lyu, Houston, TX (US); Yongquan Ye, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 682 days.

(21) Appl. No.: 17/304,652

(22) Filed: Jun. 24, 2021

(65) Prior Publication Data
US 2022/0409083 A1   Dec. 29, 2022

(51) Int. Cl.
*A61B 5/055* (2006.01)
*G01R 33/48* (2006.01)
*G01R 33/561* (2006.01)

(52) U.S. Cl.
CPC .......... *A61B 5/055* (2013.01); *G01R 33/4822* (2013.01); *G01R 33/4826* (2013.01); *G01R 33/5611* (2013.01)

(58) Field of Classification Search
CPC ................ A61B 5/055; G01R 33/4822; G01R 33/4826; G01R 33/5611
See application file for complete search history.

(56) References Cited

U.S. PATENT DOCUMENTS

| | | | |
|---|---|---|---|
| 2013/0099784 A1* | 4/2013 | Setsompop | G01R 33/543 324/309 |
| 2015/0077112 A1* | 3/2015 | Otazo | A61B 5/7207 324/318 |
| 2018/0143277 A1* | 5/2018 | Chen | G01R 33/5611 |
| 2018/0189930 A1* | 7/2018 | Dannels | G01R 33/5619 |
| 2019/0250237 A1 | 8/2019 | Boernert et al. | |
| 2020/0090382 A1* | 3/2020 | Huang | G06N 3/084 |
| 2020/0357149 A1* | 11/2020 | Nagashima | G06T 11/006 |
| 2020/0405176 A1 | 12/2020 | Nielsen et al. | |
| 2021/0247477 A1* | 8/2021 | Takeshima | G01R 33/5635 |

OTHER PUBLICATIONS

Jesse Hamilton et al., Recent Advances in Parallel Imaging for MRI, Progress in Nuclear Magnetic Resonance Spectroscopy, 101: p. 1-p. 60, 2017.
Daniel K. Sodickson et al., Simultaneous Acquisition of Spatial Harmonics Simultaneous Acquisition of Spatial Harmonics (SMASH): Fast Imaging with Radiofrequency Coil Arrays, Magnetic Resonance in Medicine, 38(4): 591-603, 1997.

(Continued)

*Primary Examiner* — Sean A Frith
(74) *Attorney, Agent, or Firm* — METIS IP LLC

(57) ABSTRACT

The present disclosure is related to systems and methods for magnetic resonance imaging (MRI). The method includes obtaining a plurality of target sets of k-space data by filling target MR signals acquired by a plurality of coils of an MRI device into k-space along a corkscrew trajectory. The method includes obtaining a coil sensitivity of each of the plurality of coils. The method includes obtaining a point spread function corresponding to the corkscrew trajectory. The method includes generating a target image based on an objective function.

20 Claims, 9 Drawing Sheets

(56) References Cited

OTHER PUBLICATIONS

Klaas P. Pruessmann et al., SENSE: Sensitivity Encoding for Fast MRI, Magnetic Resonance in Medicine, 42(5): 952-962, 1999.
Mark A. Griswold et al., Generalized Autocalibrating Partially Parallel Acquisitions (GRAPPA), Magnetic Resonance in Medicine, 47(6): 1202-1210, 2002.
Berkin Bilgic et al., Wave-CAIPI for Highly Accelerated 3D Imaging, Magnetic Resonance in Medicine, 73(6): p. 1-p. 26, 2015.
Felix A. Breuer et al., Controlled Aliasing in Volumetric Parallel Imaging (2D Caipirinha), Magnetic Resonance in Medicine, 55(3): 549-556, 2006.
Hisamoto Moriguchi et al., Bunched Phase Encoding (Bpe): A New Fast Data Acquisition Method in MRI, Magnetic Resonance in Medicine, 55(3): 633-648, 2006.

* cited by examiner

SYSTEMS AND METHODS FOR MAGNETIC RESONANCE IMAGING

TECHNICAL FIELD

This disclosure generally relates to magnetic resonance imaging (MRI), and more particularly, relates to systems and methods for image reconstruction in MRI.

BACKGROUND

Magnetic resonance imaging (MRI) systems are widely used in medical diagnose. MRI systems use a powerful magnetic field and radio frequency (RF) techniques to generate images of a subject to be scanned. Parallel imaging may be employed to accelerate data acquisition in MRI using an array of receive coils with spatially-varying sensitivities. However, the acceleration in parallel imaging may be limited by a noise amplification in the reconstruction, which may increase non-linearly with an increase in the acceleration factor that relates to the extent of acceleration in parallel imaging. Thus, it is desirable to provide systems and methods for efficiently reconstructing a high-quality MRI image with a relatively high acceleration factor.

SUMMARY

According to an aspect of the present disclosure, a method for MRI may be implemented on a computing device having at least one processor and at least one storage device. The method may include obtaining a plurality of target sets of k-space data by filling target MR signals acquired by a plurality of coils of an MRI device into k-space along a corkscrew trajectory. The method may include obtaining a coil sensitivity of each of the plurality of coils. The method may include obtaining a point spread function corresponding to the corkscrew trajectory. The method may include generating a target image based on an objective function. The objective function may be determined based on an operator, the plurality of target sets of k-space data, the plurality of coil sensitivities, and the point spread function. The operator may represent a mapping relationship between the target image and the plurality of target sets of k-space data.

In some embodiments, the plurality of target sets of k-space data may be obtained by filling the target MR signals into the k-space with variable densities.

In some embodiments, the method may include generating a first image based on a first set of k-space data, wherein the first set of k-space data is obtained by filling reference MR signals into the k-space along a reference trajectory. The method may include generating a second image based on a second set of k-space data, wherein the second set of k-space data is obtained by filling the reference MR signals into the k-space along the corkscrew trajectory. The method may include determining the point spread function based on the first image and the second image.

In some embodiments, the method may include, for the each target set of k-space data of the plurality of target sets of k-space data, obtaining the target MR signals acquired by the coil of the plurality of coils of the MRI device. The method may include obtaining a mask. The method may include obtaining the target set of k-space data based on the target MR signals and the mask.

In some embodiments, the method may include setting the target image as an independent variable in the objective function.

In some embodiments, the method may include determining the operator based on the plurality of coil sensitivities, the point spread function, and the mask. The method may include determining an aliased image based on the plurality of target sets of k-space data, the plurality of coil sensitivities, and the point spread function. The method may include determining the objective function based on the operator and the aliased image.

In some embodiments, the method may include, for each coil of the plurality of coils of the MRI device, generating a first candidate image related to the coil based on a coil sensitivity of the coil and the target image. The method may include determining a first candidate set of k-space data based on the first candidate image, the point spread function, and the mask. The method may include generating a second candidate image related to the coil by processing the first candidate set of k-space data based on the point spread function and the coil sensitivity of the coil. The method may include determining the operator based on a plurality of second candidate images related to the plurality of coils.

In some embodiments, the k-space may be three-dimensional. The first candidate image may be a three-dimensional image. The method may include generating a first processed candidate image by performing a first Fourier transform on the first candidate image along a first direction of the k-space. The method may include generating a second processed candidate image by multiplying the point spread function and the first processed candidate image. The method may include generating a third processed candidate image by performing a second Fourier transform on the second processed candidate image along a second direction of the k-space. The method may include generating a second candidate set of k-space data by performing a third Fourier transform on the third processed candidate image along a third direction of the k-space. The method may include generating the first candidate set of k-space data based on the second candidate set of k-space data and the mask, wherein the first direction, the second direction, and the third direction are orthogonal to each other.

In some embodiments, the method may include generating a first processed candidate set of k-space data by performing a first inverse Fourier transform on the first candidate set of k-space data along the third direction of the k-space. The method may include generating a second processed candidate set of k-space data by performing a second inverse Fourier transform on the first processed candidate set of k-space data along the second direction of the k-space. The method may include generating a third processed candidate set of k-space data by multiplying the second processed candidate set of k-space data and a conjugation of the point spread function. The method may include generating a third candidate image by performing a third inverse Fourier transform on the third processed candidate set of k-space data along the first direction of the k-space. The method may include generating the second candidate image by multiplying the third candidate image and a conjugation of the coil sensitivity of the coil.

In some embodiments, the k-space may be three-dimensional. The target set of k-space data may be three-dimensional. The method may include, for the each target set of k-space data of the plurality of target sets of k-space data, generating a first processed target set of k-space data by performing a first inverse Fourier transform on the target set of k-space data along a third direction of the k-space. The method may include generating a second processed target set of k-space data by performing a second inverse Fourier transform on the first processed target set of k-space data along a second direction of the k-space. The method may include generating a third processed target set of k-space data by multiplying the second processed target set of k-space data and a conjugation of the point spread function. The method may include generating a first intermediate image related to a coil corresponding to the target set of k-space data by performing a third inverse Fourier transform on the third processed target set of k-space data along a first direction of the k-space. The method may include generating a second intermediate image related to the coil based on a coil sensitivity of the coil and the first intermediate image. The method may include generating the aliased image based on a plurality of second intermediate images related to the plurality of coils.

In some embodiments, the method may include determining the target image based on the objective function according to a conjugate gradient algorithm.

In some embodiments, the method may include obtaining the plurality of target sets of k-space data by filling the target MR signals acquired by the plurality of coils of the MRI device into the k-space along a random corkscrew trajectory.

According to another aspect of the present disclosure, a system for MRI may include at least one storage device storing a set of instructions, and at least one processor in communication with the at least one storage device. When executing the stored set of instructions, the at least one processor may cause the system to perform a method. The method may include obtaining a plurality of target sets of k-space data by filling target MR signals acquired by a plurality of coils of an MRI device into k-space along a corkscrew trajectory. The method may include obtaining a coil sensitivity of each of the plurality of coils. The method may include obtaining a point spread function corresponding to the corkscrew trajectory. The method may include generating a target image based on an objective function. The objective function may be determined based on an operator, the plurality of target sets of k-space data, the plurality of coil sensitivities, and the point spread function. The operator may represent a mapping relationship between the target image and the plurality of target sets of k-space data.

According to still another aspect of the present disclosure, a method for MRI may be implemented on a computing device having at least one processor and at least one storage device. The method may include obtaining a plurality of target sets of k-space data by filling target MR signals acquired by a plurality of coils of an MRI device into k-space along a corkscrew trajectory. The method may include determining an aliased image related to the plurality of coils based on the plurality of target sets of k-space data. The method may include determining a target image based on the aliased image and a mapping relationship between the target image and the aliased image.

In some embodiments, the method may include determining an objective function based on the mapping relationship and the aliased image. The method may include generating the target image by solving the objective function iteratively.

In some embodiments, the method may include determining the mapping relationship based on a plurality of coil sensitivities, a point spread function corresponding to the corkscrew trajectory, and a mask corresponding to the corkscrew trajectory.

In some embodiments, the method may include determining a plurality of intermediate images corresponding to the plurality of coils based on the plurality of target sets of k-space data, the plurality of coil sensitivities, and the point spread function. The method may include generating the aliased image based on the plurality of intermediate images corresponding to the plurality of coils.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
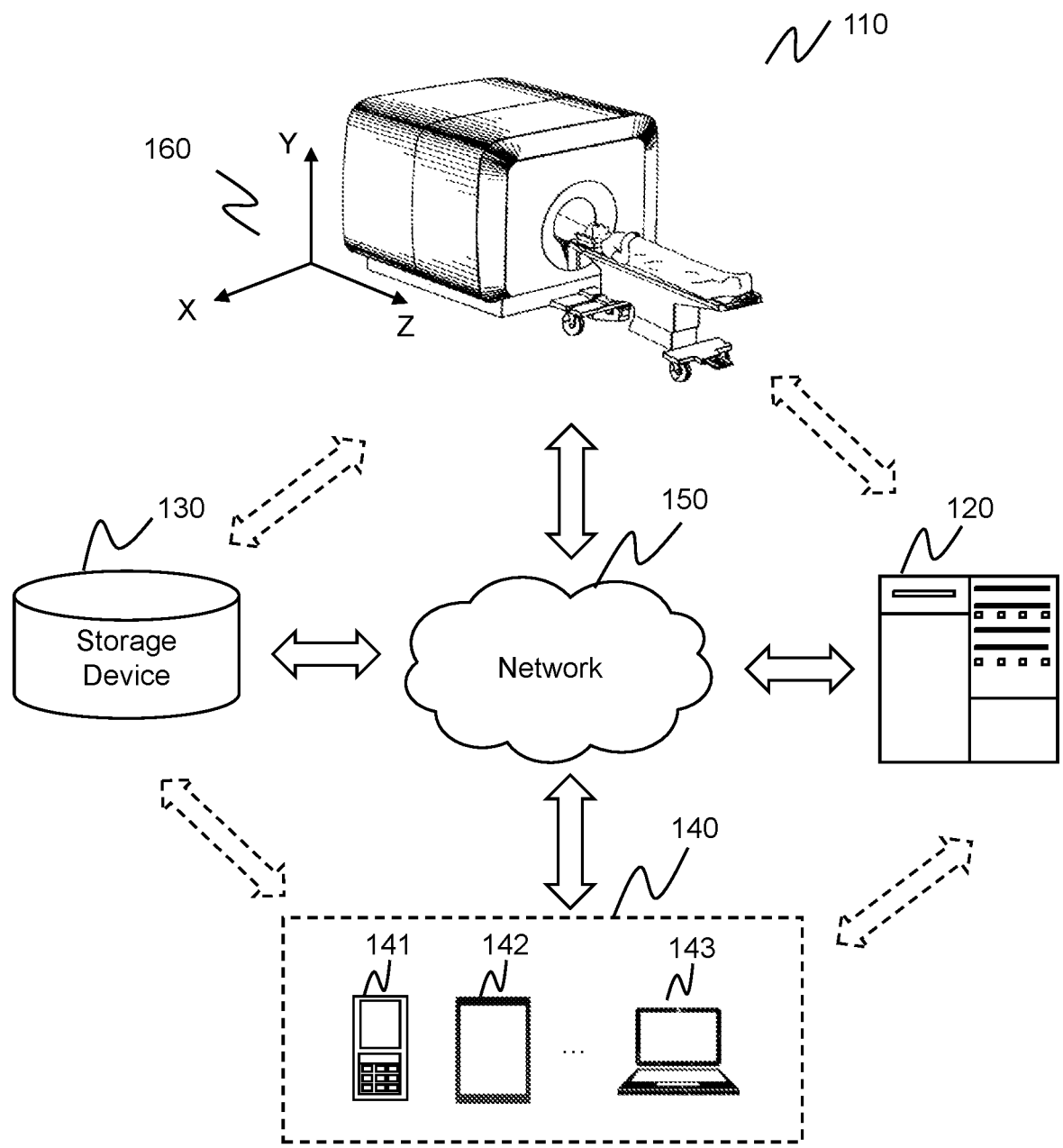
FIG. 1 is a schematic diagram illustrating an exemplary MRI system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

The term "pixel" and "voxel" in the present disclosure are used interchangeably to refer to an element in an image. The term "image" in the present disclosure is used to refer to images of various forms, including a 2-dimensional image, a 3-dimensional image, a 4-dimensional image, etc.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in inverted order, or simultaneously. Moreover, one or more other operations may be added to the flowcharts. One or more operations may be removed from the flowcharts.

Moreover, while the systems and methods disclosed in the present disclosure are described primarily regarding image reconstruction in an MRI system. It should be understood that this is only for illustration purposes. The systems and methods of the present disclosure may be applied to any other kind of medical imaging system. In some embodiments, the imaging system may include a single modality imaging system and/or a multi-modality imaging system. The single modality imaging system may include, for example, the MRI system. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc.

MRI is an imaging technique used in radiology to capture images of an anatomy or a physiological process of a subject (e.g., a patient, or a body part thereof). MRI is based on the phenomenon of a nuclear magnetic resonance (NMR). In a typical MRI scan, a subject may be placed inside a strong static main magnetic field. MRI signals may be generated by applying an RF pulse to excite the spin of the atomic nucleus in the subject. Following the excitation, the subject may emit a decaying RF signal that can be detected in the form of radiofrequency voltage in a receiver coil. In order to distinguish the received signals from different spatial positions, additional magnetic field gradients may be superimposed on the main magnetic field so that the field strength varies with spatial position, allowing the origins of MRI signals emitted from the subject to be localized. Based on a gradient encoding, a Fourier imaging may be performed, in which measurements representing the spatial frequency of the subject, termed as k-space, can be acquired using a specific sampling trajectory. A common acquisition scheme is a Cartesian sampling, and an image reconstruction is performed by applying an inverse Fourier transform (e.g., inverse fast Fourier transform) on k-space data. However, Fourier imaging is the relatively slow in terms of its data acquisition speed, in which only limited k-space positions can be encoded per unit time and this process has to be sequentially repeated until the entire k-space region for the target spatial resolution is sampled. Such a low imaging speed not only increases patient discomfort, but also imposes limits on spatiotemporal resolution and volumetric coverage.

An alternative approach to increase the imaging speed in MRI is to accelerate MRI data acquisition by collecting fewer phase-encoding lines in the k-space. A variety of parallel imaging techniques, such as a simultaneous acquisition of spatial harmonics (SMASH), a sensitivity encoding (SENSE), and a generalized autocalibrating partially parallel acquisition (GRAPPA), have been employed to accelerate the data acquisition in MRI using an array of receiver coils with spatially-varying sensitivities. MRI signals may be acquired using an array of independent receiver channels. A receiver coil may be more sensitive to a specific volume of tissue closer to the receiver coil, which means that the receiver coils may provide an additional source of spatial information for image reconstruction. The k-space data may be undersampled in the phase-encoding direction (and potentially also the partition-encoding direction in 3D imaging) to reduce the scan time. However, the acceleration in parallel imaging may be limited by noise amplification in the reconstruction, which may increase non-linearly with an increase in the acceleration factor.

Figure 9A:
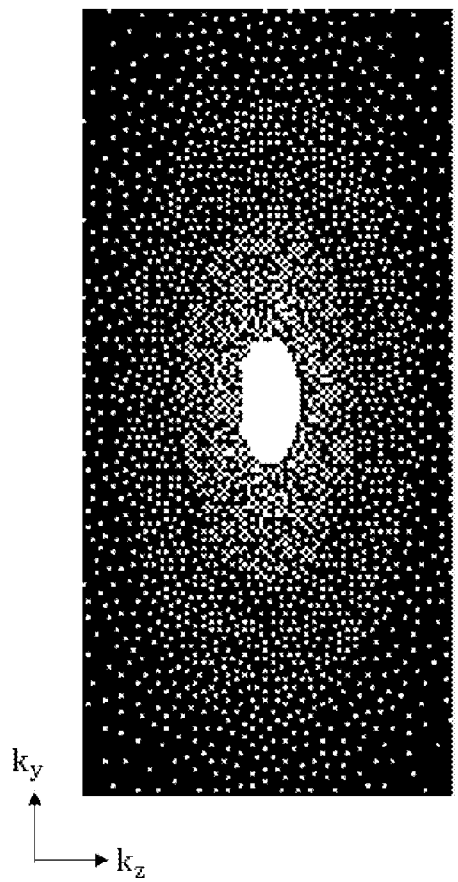
FIG. 9A is a schematic diagram illustrating an exemplary variable density sampling pattern according to some embodiments of the present disclosure.
Figure 9B:
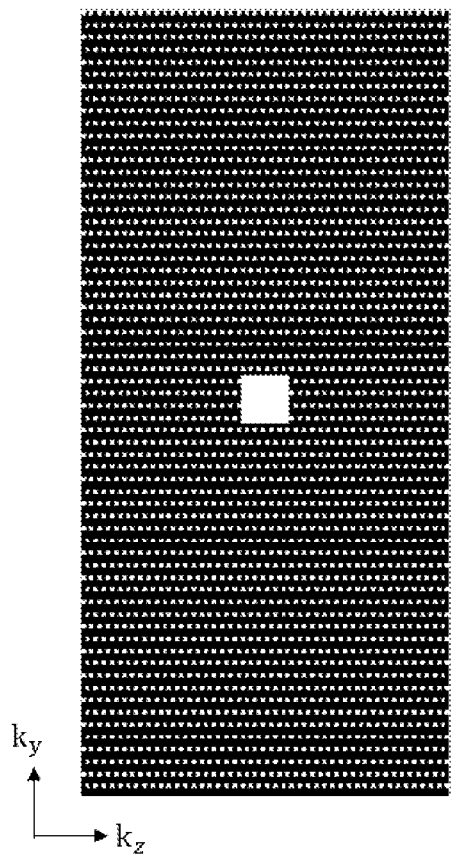
FIG. 9B is a schematic diagram illustrating an exemplary CAIPIRINHA sampling pattern according to some embodiments of the present disclosure.

A wave-controlled aliasing in parallel imaging (CAIPI) acquisition and reconstruction technique involves applying sinusoidal gy and gz gradients during the readout of each Kx encoding line. A uniform undersampling pattern (e.g., a controlled aliasing in parallel imaging results in higher acceleration (CAIPIRINHA) sampling pattern) may be used in the wave-CAIPI acquisition and reconstruction technique. For example, the CAIPIRINHA sampling may use a group of distinctive k-space sampling patterns to reduce aliasing artifacts (i.e., aliasing pixels) in reconstructed images. The acquired k-space samplings may be offset from the normal grid-like sampling by shifting the sampling positions of alternate rows with respect to the partition-encoding direction, as illustrated in FIG. 9B. The acceleration factor of the CAIPIRINHA sampling may be a multiple of 2, for example, two, four, six, or the like. By using the uniform undersampling pattern, there is an analytical solution for determining a reconstructed image, and there is no need to use an iterative algorithm to determine the reconstructed image, the speed of image reconstruction may be fast. In addition, the quality of a reconstructed image may be good when the acceleration factor is relatively low (e.g., lower than 4). However, the acceleration factor of the uniform undersampling pattern may be inflexible (e.g., the acceleration factor being always a multiple of 2), and the reconstructed image may have significant artifacts when the acceleration factor is relatively high (e.g., greater than 4). In some embodiments, in one MRI data acquisition, the acceleration factor may be fixed.

The variable density undersampling may have a potential in reducing aliasing artifacts and improving sampling efficiency. In some embodiments, the variable density undersampling may allow the sampling density to be a function of the k-space location, as illustrated in FIG. 9A. This may enable a flexible allocation of the scan time based on signal characteristics, scan time constraints, and/or the image quality suitable for a specific application. Data in the central k-space region may correspond to structural features associated with a subject to be scanned, and data in the outer k-space region may correspond to detailed features associated with the subject. In some embodiments, the variable density undersampling may sufficiently sample the central k-space region to reduce low-frequency aliasing artifacts, and undersample the outer k-space region to reduce the scan time while maintaining or increasing the image quality in terms of, e.g., the spatial resolution. For example, the sampling density in the central k-space region may be relatively high, and the sampling density in the outer k-space region may be relatively low. As used herein, a sampling density refers to a number (or count) of sampled data points per unit area of the k-space. The acceleration factor of the variable density undersampling for different portions of the k-space may be any value, for example, 2, 3, 4, 5, 6, 10, or the like. In some embodiments, the acceleration factor of an undersampling pattern, e.g., a variable density undersampling pattern, a uniform undersampling pattern, may be a ratio of the amount of k-space data needed for a fully sampled k-space to the amount of k-space data sampled according to the undersampling pattern. However, existing wave-CAIPI acquisition and reconstruction techniques do not support such a variable density undersampling pattern.

For illustration purposes, for rectilinear 3D imaging with phase and partition encoding (i.e., the slice selection encoding), the received signal may be expressed using the k-space notation at fixed Ky and Kz as Equation (1):

$$s(t)=\int_{x,y,z}m(x,y,z)e^{-i2\pi[k_x(t)x+k_yu+k_zz]}dxdydz, \quad (1)$$

where m(x, y, z) refers to an underlying image (i.e., a reconstructed image); Kx refers to a frequency encoding; Ky refers to a phase encoding; and Kz refers to a slice selection encoding. When additional sinusoidal wave gradients $g_y$ and gz are applied during each readout line in a Y-axis and a Z-axis (e.g., a Y-axis and a Z-axis in a coordinate system 160 illustrated in FIG. 1), the received signal may be expressed as Equation (2):

$$s(t)=\int_{x,y,z}m(x,y,z)\exp\{-iy\int_0^t[g_y(\tau)y+g_z(\tau)z]d\tau\}dxdydz, \quad (2)$$

where $g_y$ and $g_z$ refer to additional sinusoidal wave gradients. In some embodiments, Equation (2) may be rewritten more succinctly as:

$$\text{wave}[x,y,z] = F_x^{-1} Psf[k,y,z](F_x m[x,y,z]), \quad (3)$$

where wave[x, y, z] refers to an image acquired with the wave gradients; Fx refers to a discrete Fourier transform (DFT) operation in an X-axis; $F_x^{-1}$ refers to an inverse DFT operation in the X-axis; k refers to a k-space index that enumerates the data points acquired per readout line; and Psf[k, y, z] refers to a point spread function (PSF) that describes the effect of the wave gradients: each readout line in the underlying image m[x, y, z] is convolved with the PSF to yield the acquired wave image wave[x, y, z], in which the PSF is a function of spatial location (y, z). More descriptions of the X-axis, the Y-axis, and the Z-axis may be found elsewhere in the present disclosure (e.g., FIGS. 1-2, and descriptions thereof).

An aspect of the present disclosure relates to a system and method for MRI. A processing device may obtain a plurality of target sets of k-space data. Each target set of k-space data may correspond to target MR signals acquired by an RF receiver coil (also referred to as a coil for brevity in the present disclosure) of a plurality of coils of an MRI device. The each target set of k-space data may be obtained by filling the target MR signals into k-space along a corkscrew trajectory. In some embodiments, the target set of k-space data may be obtained by filling the target MR signals into the k-space along a variable density corkscrew trajectory or a random corkscrew trajectory. As used herein, a variable density corkscrew trajectory refers to that a plurality of corkscrew trajectories corresponding to a target set of k-space data are distributed in the k-space with variable densities. As used herein, a random corkscrew trajectory refers to that a plurality of corkscrew trajectories corresponding to a target set of k-space data are randomly distributed in the k-space. The processing device may obtain a coil sensitivity of each of the plurality of coils. The processing device may obtain a point spread function corresponding to the corkscrew trajectory. The processing device may generate a target image based on an objective function. The objective function may be determined based on an operator, the plurality of target sets of k-space data, the plurality of coil sensitivities, and the point spread function. The operator may represent a mapping relationship between the target image and the plurality of target sets of k-space data.

Accordingly, a variable-density wave acquisition and reconstruction method may be provided in the present disclosure. As used herein, a variable-density wave acquisition and reconstruction refers to that k-space data used for MRI image reconstruction is obtained by filling MR signals into the k-space along a variable density corkscrew trajectory. Since the acceleration factor of the variable density undersampling can be any suitable value, the setting of the acceleration factor in the variable-density wave acquisition and reconstruction algorithm may be relatively flexible. In addition, when the acceleration factor is the same (especially when the acceleration factor is relatively high, e.g., higher than 6) as a uniform undersampling pattern (e.g., the CAIPIRINHA sampling pattern), the quality of the target image (e.g., a signal-to-noise ratio of the target image) generated based on k-space data obtained using the variable-density undersampling pattern may be relatively high compared to the uniform undersampling pattern. Since the uniform undersampling does not consider the conjugate symmetry of the K-space data, and the variable density undersampling can sufficiently sample the central k-space region (i.e., a low frequency region) and undersample a conjugate symmetry region, the efficiency of the variable density sampling may be relatively high, and the quality of the target image generated based on k-space data obtained using the variable-density undersampling pattern may be relatively high compared to the uniform undersampling pattern.

Furthermore, a random wave acquisition and reconstruction method may also be provided in the present disclosure. As used herein, a random wave acquisition and reconstruction refers to that k-space data used for MRI image reconstruction is obtained by filling MR signals into the k-space along a random corkscrew trajectory. A compressed sensing technique may be used in the reconstruction of a target image for correcting random artifacts generated in the random undersampling (i.e., the random corkscrew trajectory), which may further improve the quality of the target image.

FIG. 1 is a schematic diagram illustrating an exemplary MRI system according to some embodiments of the present disclosure. As illustrated, an MRI system 100 may include an MRI device 110, a processing device 120, a storage device 130, a terminal 140, and a network 150. The components of the MRI system 100 may be connected in one or more of various ways. Merely by way of example, as illustrated in FIG. 1, the MRI device 110 may be connected to the processing device 120 directly as indicated by the bi-directional arrow in dotted lines linking the MRI device 110 and the processing device 120, or through the network 150. As another example, the storage device 130 may be connected to the MRI device 110 directly as indicated by the bi-directional arrow in dotted lines linking the MRI device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

The MRI device 110 may be configured to scan a subject (or a part of the subject) to acquire image data, such as echo signals (or MRI signals) associated with the subject. For example, the MRI device 110 may detect a plurality of echo signals by applying an MRI pulse sequence on the subject. In some embodiments, the MRI device 110 may include, for example, a main magnet, a gradient coil (or also referred to as a spatial encoding coil), a radio frequency (RF) coil, etc., as described in connection with FIG. 2. In some embodiments, the MRI device 110 may be a permanent magnet MRI scanner, a superconducting electromagnet MRI scanner, a resistive electromagnet MRI scanner, etc., according to types of the main magnet. In some embodiments, the MRI device 110 may be a high-field MRI scanner, a mid-field MRI scanner, a low-field MRI scanner, etc., according to the intensity of the magnetic field.

The subject scanned by the MRI device 110 may be biological or non-biological. For example, the subject may include a patient, a man-made object, etc. As another example, the subject may include a specific portion, an organ, tissue, and/or a physical point of the patient. Merely by way of example, the subject may include the head, the brain, the neck, a body, a shoulder, an arm, the thorax, the heart, the stomach, a blood vessel, soft tissue, a knee, a foot, or the like, or any combination thereof.

For illustration purposes, a coordinate system 160 including an X-axis, a Y-axis, and a Z-axis may be provided in FIG. 1. The X-axis and the Z axis shown in FIG. 1 may be horizontal, and the Y-axis may be vertical. As illustrated, the positive X direction along the X-axis may be from the right side to the left side of the MRI device 110 seen from the direction facing the front of the MRI device 110; the positive Y direction along the Y-axis shown in FIG. 1 may be from the lower part to the upper part of the MRI device 110; the positive Z direction along the Z-axis shown in FIG. 1 may refer to a direction in which the subject is moved out of a scanning channel (or referred to as a bore) of the MRI device 110.

In some embodiments, the MRI device 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for image reconstruction. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the MRI device 110 may be found elsewhere in the present disclosure. See, e.g., FIG. 2 and the description thereof.

The processing device 120 may process data and/or information obtained from the MRI device 110, the storage device 130, and/or the terminal(s) 140. For example, the processing device 120 may obtain a plurality of target sets of k-space data. As another example, the processing device 120 may obtain information of a coil sensitivity of each of a plurality of coils. As another example, the processing device 120 may obtain a point spread function corresponding to a corkscrew trajectory. As still another example, the processing device 120 may generate a target image based on an objective function. In some embodiments, the processing device 120 may be a single server or a server group. The server group may be centralized or distributed. In some embodiments, the processing device 120 may be local or remote. For example, the processing device 120 may access information and/or data from the MRI device 110, the storage device 130, and/or the terminal(s) 140 via the network 150. As another example, the processing device 120 may be directly connected to the MRI device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the MRI device 110.

The storage device 130 may store data, instructions, and/or any other information. In some embodiments, the storage device 130 may store data obtained from the MRI device 110, the processing device 120, and/or the terminal(s) 140. The data may include image data acquired by the processing device 120, algorithms and/or models for processing the image data, etc. For example, the storage device 130 may store a plurality of target sets of k-space data obtained from an MRI device (e.g., the MRI device 110). As another example, the storage device 130 may store information of a coil sensitivity of each of a plurality of coils. As still another example, the storage device 130 may store a point spread function determined by the processing device 120. As still another example, the storage device 130 may store an objective function determined by the processing device 120. As still another example, the storage device 130 may store a target image determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the MRI system 100 (e.g., the processing device 120, the terminal(s) 140). One or more components in the MRI system 100 may access the data or instructions stored in the storage device 130 via the network 150. In some embodiments, the storage device 130 may be integrated into the MRI device 110.

The terminal(s) 140 may be connected to and/or communicate with the MRI device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the MRI system 100. In some embodiments, one or more components of the MRI system 100 (e.g., the MRI device 110, the processing device 120, the storage device 130, the terminal(s) 140, etc.) may communicate information and/or data with one or more other components of the MRI system 100 via the network 150. For example, the processing device 120 and/or the terminal 140 may obtain a plurality of target sets of k-space data from the MRI device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MRI device 110. As another example, a component of the MRI system 100 may be replaced by another component that can implement the functions of the component.

Figure 2:
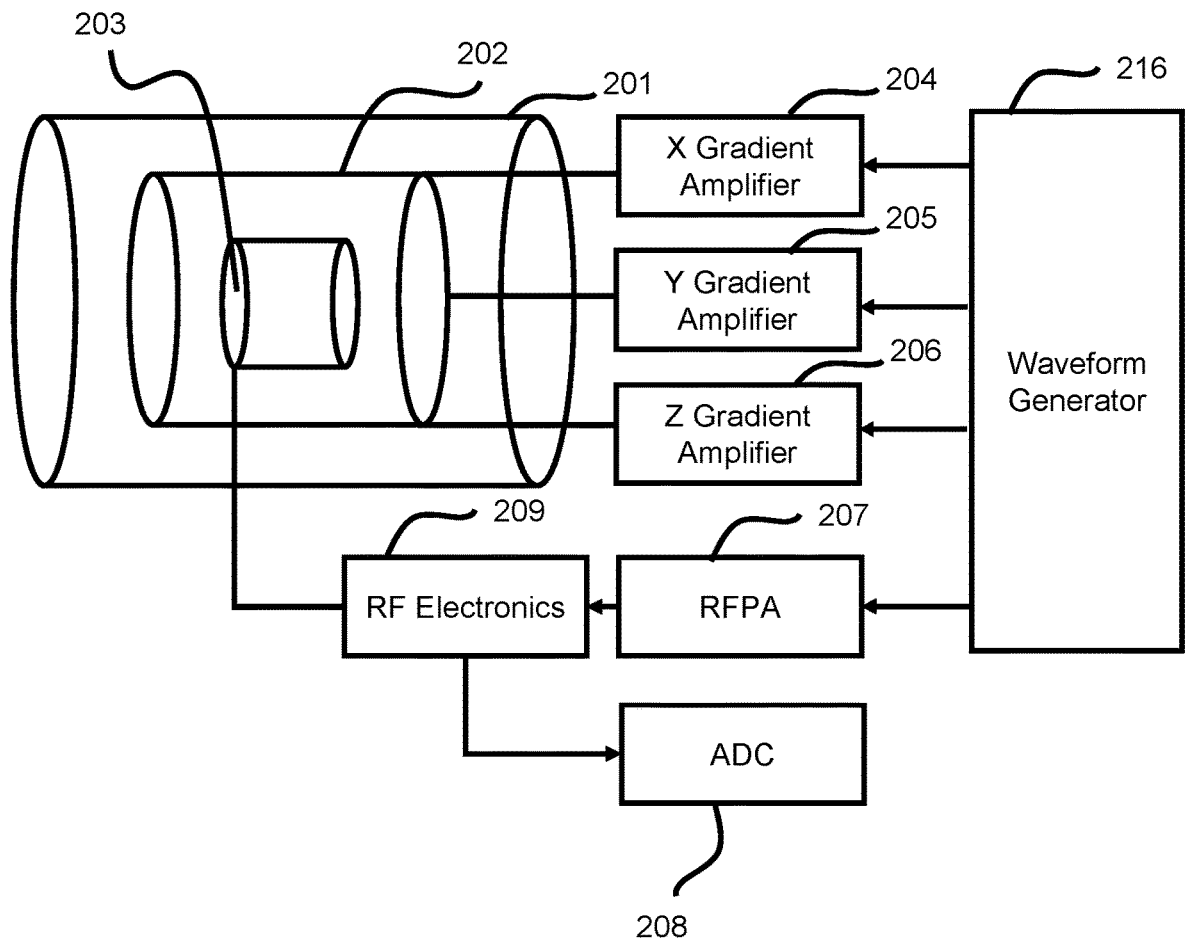
FIG. 2 is a schematic diagram illustrating an exemplary MRI device 110 according to some embodiments of the present disclosure.

FIG. 2 is a schematic diagram illustrating an exemplary MRI device 110 according to some embodiments of the present disclosure. One or more components of the MRI device 110 are illustrated in FIG. 2. As illustrated, a main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore that the subject is placed within. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of a subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or waveform receiver. The RF electronics 209 may be connected to a radiofrequency power amplifier (RFPA) 207 and an analog-to-digital converter (ADC) 208.

In some embodiments, the RF coils 203 may include one or more RF transmit coils and/or one or more RF receiver coils. The RF transmit coil(s) may transmit RF pulses to the subject. Under the coordinated action of the main magnetic field, the gradient magnetic field, and the RF pulses, MR signals relating to the subject may be generated according to a pulse sequence. The RF receiver coils may acquire MR signals from the subject according to the pulse sequence. In some embodiments, an RF receiver coil may correspond to a channel for acquiring MR signals. The RF receiver coils may receive a plurality of channels of MRI signals from the subject.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated by the subject may be sensed by the RF coils 203. The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI device 110 may further include a subject positioning system (not shown). The subject positioning system may include a subject cradle and a transport device. The subject may be placed on the subject cradle and be positioned by the transport device within the bore of the main magnet 201.

MRI systems (e.g., the MRI system 100 disclosed in the present disclosure) may be commonly used to obtain an interior image from a patient for a particular region of interest (ROI) that can be used for the purposes of, e.g., diagnosis, treatment, or the like, or a combination thereof. MRI systems include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MRI image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct an image in accordance with the MRI imaging protocol that is used.

Figure 3:
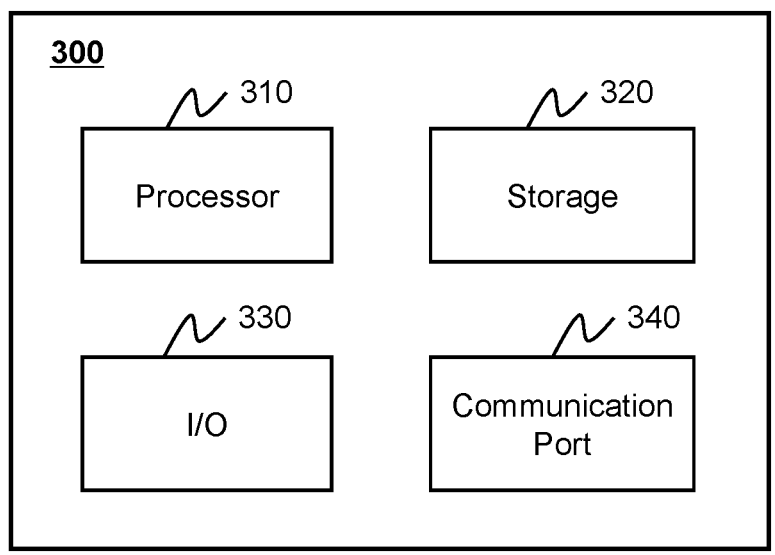
FIG. 3 is a schematic diagram illustrating exemplary hardware and/or software components of a computing device 300 according to some embodiments of the present disclosure.

FIG. 3 is a schematic diagram illustrating exemplary hardware and/or software components of a computing device 300 according to some embodiments of the present disclosure. In some embodiments, one or more components of the MRI system 100 may be implemented on one or more components of the computing device 300. Merely by way of example, the processing device 120 and/or the terminal(s) 140 may be implemented one or more components of the computing device 300, respectively.

As illustrated in FIG. 3, the computing device 300 may include a processor 310, a storage device 320, an input/output (I/O) 330, and a communication port 340. The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process image data of a subject obtained from the MRI device 110, the storage device 130, terminal(s) 140, and/or any other component of the MRI system 100.

In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage device 320 may store data/information obtained from the MRI device 110, the storage device 130, the terminal(s) 140, and/or any other component of the MRI system 100. In some embodiments, the storage device 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 320 may store one or more programs and/or instructions to perform exemplary methods described in the present disclosure.

The I/O 330 may input and/or output signals, data, information, etc. In some embodiments, the I/O 330 may enable a user interaction with the computing device 300 (e.g., the processing device 120). In some embodiments, the I/O 330 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 340 may be connected to a network (e.g., the network 150) to facilitate data communications. The communication port 340 may establish connections between the computing device 300 (e.g., the processing device 120) and one or more components of the MRI system 100 (e.g., the MRI device 110, the storage device 130, and/or the terminal(s) 140). The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
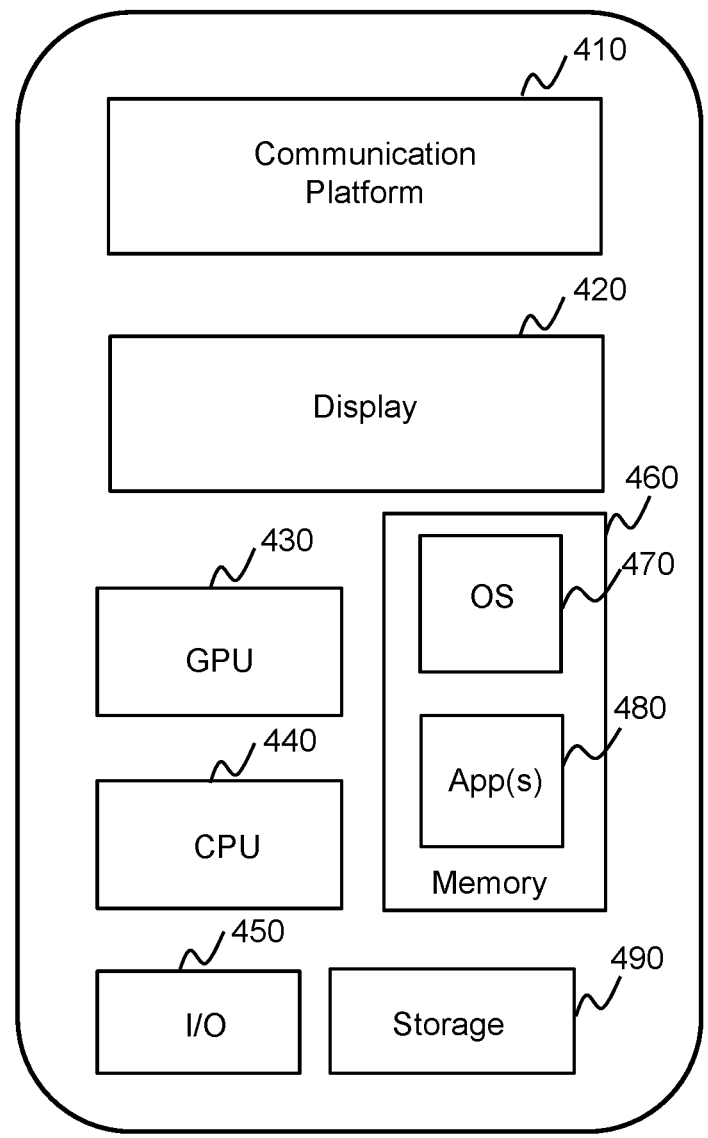
FIG. 4 is a schematic diagram illustrating exemplary hardware and/or software components of a mobile device 400 may be implemented according to some embodiments of the present disclosure.

FIG. 4 is a schematic diagram illustrating exemplary hardware and/or software components of a mobile device 400 may be implemented according to some embodiments of the present disclosure. In some embodiments, one or more components of the MRI system 100 may be implemented on one or more components of the mobile device 400. Merely by way of example, the terminal 140 may be implemented on one or more components of the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to the MRI system 100. User interactions with the information stream may be achieved via the I/O 450 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal. A computer may also act as a server if appropriately programmed.

Figure 5:
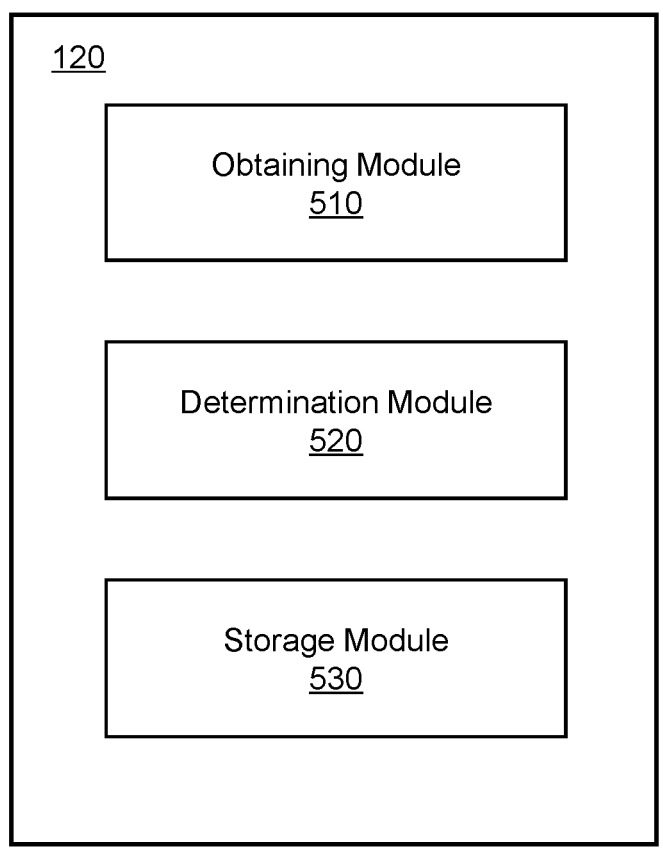
FIG. 5 is a schematic diagram illustrating an exemplary processing device according to some embodiments of the present disclosure.

FIG. 5 is a schematic diagram illustrating an exemplary processing device according to some embodiments of the present disclosure. In some embodiments, the processing device 120 may include an obtaining module 510, a determination module 520, and a storage module 530. In some embodiments, the modules may be hardware circuits of all or part of the processing device 120. The modules may also be implemented as an application or set of instructions read and executed by the processing device 120. Further, the modules may be any combination of the hardware circuits and the application/instructions. For example, the modules may be part of the processing device 120 when the processing device 120 is executing the application/set of instructions.

The obtaining module 510 may be configured to obtain data and/or information associated with the MRI system 100. The data and/or information associated with the MRI system 100 may include a plurality of target sets of k-space data, a coil sensitivity of each of a plurality of coils, a point spread function, an objective function, a target image, or the like, or any combination thereof. For example, the obtaining module 510 may obtain a plurality of target sets of k-space data. As another example, the obtaining module 510 may obtain a coil sensitivity of each of a plurality of coils. As still another example, the obtaining module 510 may obtain a point spread function corresponding to a corkscrew trajectory. In some embodiments, the obtaining module 510 may obtain the data and/or the information associated with the MRI system 100 from one or more components (e.g., the MRI device 110, the storage device 130, the terminal 140) of the MRI system 100 via the network 150.

The determination module 520 may be configured to determine data and/or information associated with the MRI system 100. In some embodiments, the determination module 520 may determine an objective function. For example, the determination module 520 may determine an operator based on a plurality of coil sensitivities, a point spread function, and a mask. The determination module 520 may determine an aliased image based on a plurality of target sets of k-space data, the plurality of coil sensitivities, and the point spread function. The determination module 520 may determine an objective function based on the operator and the aliased image. More descriptions for determining the objective function may be found elsewhere in the present disclosure (e.g., FIGS. 6, and 7, and descriptions thereof). In some embodiments, the determination module 520 may generate a target image based on an objective function. More descriptions for generating the target image may be found elsewhere in the present disclosure (e.g., FIGS. 6, and 7, and descriptions thereof).

The storage module 530 may be configured to store data and/or information associated with the MRI system 100. For example, the storage module 530 may store a plurality of target sets of k-space data, a coil sensitivity of each of a plurality of coils, a point spread function, an objective function, a target image, or the like, or any combination thereof.

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the obtaining module 510 and the determination module 520 may be combined into a single module. In some embodiments, one or more modules may be added or omitted in the processing device 120. For example, the storage module 530 may be omitted.

Figure 6:
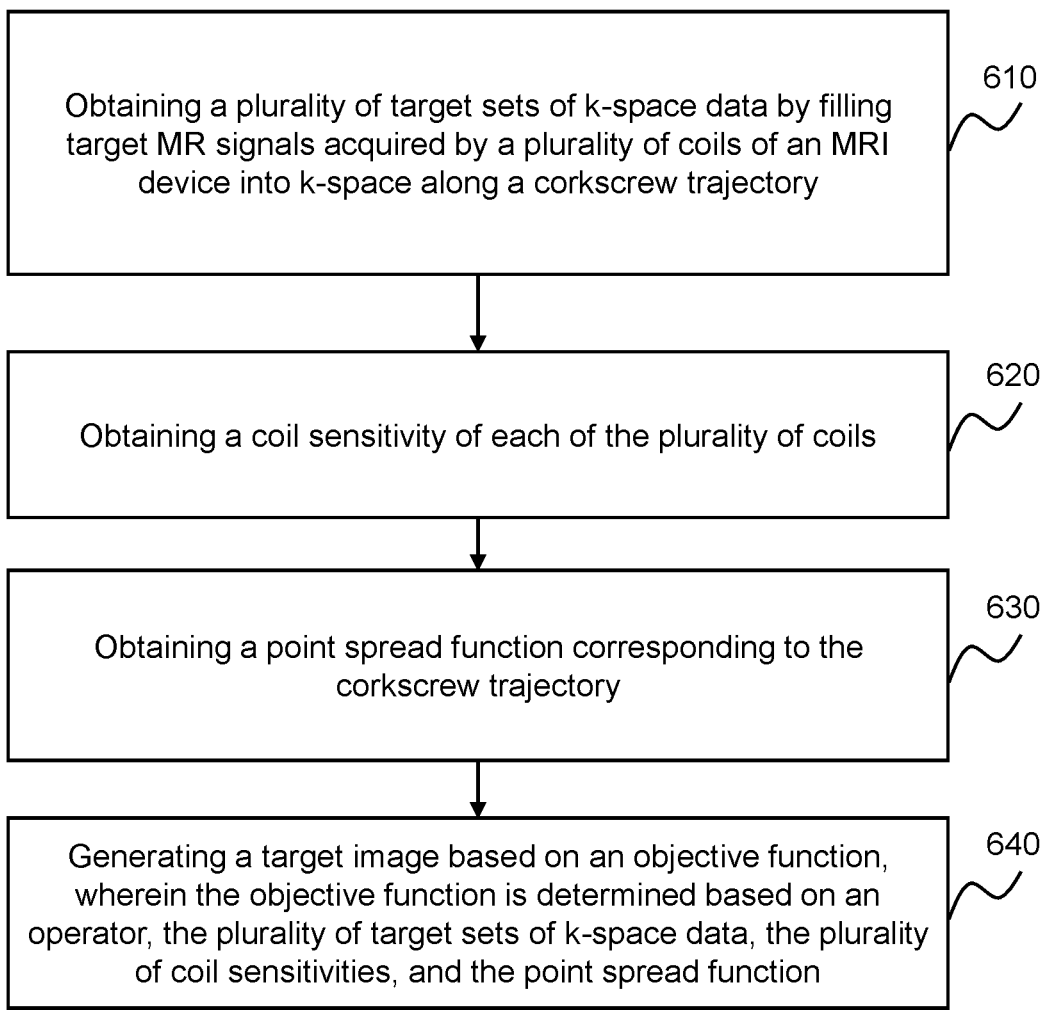
FIG. 6 is a flowchart illustrating an exemplary process for determining a target image according to some embodiments of the present disclosure.

FIG. 6 is a flowchart illustrating an exemplary process for determining a target image according to some embodiments of the present disclosure. In some embodiments, the process 600 may be implemented in the MRI system 100 illustrated in FIG. 1. For example, the process 600 may be stored in the storage device 130 and/or the storage (e.g., the storage 320, the storage 490) as a form of instructions, and invoked and/or executed by the processing device 120 (e.g., the processor 310 of the computing device 300 as illustrated in FIG. 3, the CPU 440 of the mobile device 400 as illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, the processing device 120 (e.g., the obtaining module 510) may obtain a plurality of target sets of k-space data. The plurality of target sets of k-space data may be obtained by filling target MR signals acquired by a plurality of coils of an MRI device into k-space along a corkscrew trajectory. For example, a target set of k-space data may correspond to target MR signals acquired by a coil of the plurality of coils of the MRI device (e.g., the MRI device 110). The target set of k-space data may be obtained by filling the target MR signals into k-space along the corkscrew trajectory.

In some embodiments, the processing device 120 may cause the MRI device to apply an MR pulse sequence to scan the subject. Exemplary MR pulse sequences may include a spin echo (SE) pulse sequence, a gradient echo sequences (GRE) pulse sequence, an inversion recovery (IR) pulse sequence, a multi-echo pulse sequence, or the like. Exemplary subjects may include a patient, a specific organ of the patient, a man-made object, or the like. The MRI device may include a plurality of coils configured to detect the target MRI signals (e.g., a plurality of echo signals) excited by the MR pulse sequence during the scan. A target set of k-space data may correspond to the target MR signals acquired by a coil of the plurality of coils. The processing device 120 may further determine the each target set of k-space data based on the target MRI signals detected by the corresponding coil. For example, the processing device 120 may fill the target MRI signals into a plurality of regions of the k-space (e.g., a k-space matrix) to generate the target set of k-space data.

In some embodiments, the target set of k-space data may be undersampled, i.e., only a part of a plurality of data points in the k-space may be obtained by sampling the target MRI signals, while the remaining part of the plurality of data points in the k-space may be obtained by assigning one or more values not sampled from the target MRI signals. For illustration purposes, the processing device 120 may assign the unsampled data points with one or more initial values, e.g., zero. In some embodiments, the target set of k-space data may include two-dimensional (2D) k-space data, three-dimensional (3D) k-space data, four-dimensional (4D) k-space data, or the like. As used herein, 4D k-space data refers to a data form containing 3D K-space data over time. Merely by way of example, each target set of k-space data may be a 256*256*256 digital matrix.

In some embodiments, the processing device 120 may fill the target MR signals into the k-space based on a sampling pattern or trajectory. In some embodiments, the sampling trajectory may include a Cartesian trajectory, a non-Cartesian trajectory, or the like. Exemplary non-Cartesian trajectories may include a spiral trajectory, a radial trajectory, a zigzag trajectory, a propeller trajectory, a corkscrew trajectory. In some embodiments, the sampling trajectory may include a uniform sampling trajectory, a non-uniform sampling trajectory, or the like. Exemplary non-uniform sampling trajectories may include a variable density sampling trajectory, a random sampling trajectory. For example, the target set of k-space data may be obtained by filling the target MR signals into the k-space along a uniform corkscrew trajectory, a variable density corkscrew trajectory, a random corkscrew trajectory, or the like. More descriptions of the sampling trajectory may be found elsewhere in the present disclosure (e.g., FIGS. 8A, 8B, 9A, and 9B, and descriptions thereof).

In some embodiments, the MR pulse sequence for scanning the subject may be designed based on the sampling pattern or trajectory. For example, the target MRI signals may be obtained by a wave acquisition technique as described elsewhere in the present disclosure. In the wave acquisition technique, additional sinusoidal wave gradients gy and gz may be applied during each readout line in the Y-axis and the Z-axis in the coordinate system 160, and the effect of the sinusoidal wave gradients may lead to the corkscrew sampling trajectory. Details regarding the wave acquisition technique may be found in the reference "Berkin Bilgic, et al., Wave-CAIPI for highly accelerated 3D imaging, Magn Reson Med. 2015 June; 73(6): 2152-2162," which is incorporated herein by reference.

In some embodiments, the processing device 120 may obtain the target set of k-space data based on the target MRI signals and a mask. For example, for the each target set of k-space data of the plurality of target sets of k-space data, the processing device 120 may obtain the target MR signals acquired by the coil of the plurality of coils of the MRI device. The processing device 120 may obtain a mask. Further, the processing device 120 may obtain the target set of k-space data based on the target MR signals and the mask. In some embodiments, the mask may include a 2D matrix, a 3D matrix, or the like. Each location in the mask may correspond to a data point in the k-space. For illustration purposes, the mask may include a binary matrix (e.g., a 2D binary matrix, a 3D binary matrix), where "1" means that a corresponding data point in the k-space is sampled, and "0" means that a corresponding data point in the k-space is not sampled. In some embodiments, a plurality of masks corresponding to a plurality of sampling patterns or trajectories may be stored in a storage device (e.g., the storage device 130) of the MRI system 100. For example, the plurality of masks may include a Cartesian sampling mask, a spiral sampling mask, a radial sampling mask, a corkscrew sampling mask (e.g., a variable density corkscrew sampling mask, a uniform corkscrew sampling mask, a random corkscrew sampling mask), or the like, or any combination thereof. The processing device 120 may determine the sampling pattern or trajectory based on actual needs (e.g., a type of the MRI device, a quality requirement of a reconstructed image). The processing device 120 may select the mask corresponding to the determined sampling pattern or trajectory from the plurality of masks stored in the storage device. In some embodiments, the mask corresponding to the each target set of k-space data of the plurality of target sets of k-space data may be the same.

In some embodiments, the processing device 120 may obtain the plurality of target sets of k-space data from one or more components (e.g., the MRI device 110, the terminal 140, and/or the storage device 130) of the MRI system 100 or an external storage device via the network 150. For example, the MRI device 110 may transmit the plurality of target sets of k-space data to the storage device 130, or any other storage device for storage. The processing device 120 may obtain the plurality of target sets of k-space data from the storage device 130, or any other storage device. As another example, the processing device 120 may obtain the plurality of target sets of k-space data from the MRI device 110 directly.

In 620, the processing device 120 (e.g., the obtaining module 510) may obtain a coil sensitivity of each of the plurality of coils.

In some embodiments, a coil may correspond to a coil sensitivity. As used herein, the coil sensitivity of a coil refers to a response degree of the coil for receiving an input signal (e.g., an MRI signal). In some embodiments, the coil sensitivity of a coil may represent a spatial brightness change and/or a phase change introduced when an image is obtained by the coil. In some embodiments, the coil sensitivity may be a complex number, and the modulus of the complex number may be between 0 and 1. In some embodiments, the coil sensitivity of the each coil of the plurality of coils in the MRI device may be the same or different.

In some embodiments, the coil sensitivity of the coil may be determined based on a coil sensitivity algorithm. Exemplary coil sensitivity algorithms may include a sum of squares (SOS) algorithm, an estimating signal parameters via rotational invariance technique (ESPIRiT)-based algorithm, or the like.

In some embodiments, the processing device 120 may obtain the plurality of coil sensitivities of the plurality of coils from one or more components (e.g., the MRI device 110, the terminal 140, and/or the storage device 130) of the MRI system 100 or an external storage device via the network 150. For example, the plurality of coil sensitivities of the plurality of coils may be stored in the storage device 130, or any other storage device for storage. The processing device 120 may obtain the plurality of coil sensitivities of the plurality of coils from the storage device 130, or any other storage device.

In 630, the processing device 120 (e.g., the obtaining module 510) may obtain a point spread function corresponding to the corkscrew trajectory.

In some embodiments, the point spread function may be used to characterize the effect of the wave gradients in the wave acquisition technique as described in connection with operation 610. For example, the point spread function may characterize a point (voxel or pixel) spreading effect over the whole field of view (FOV) of a reconstructed image caused by the corkscrew trajectory.

In some embodiments, the processing device 120 may generate a first image based on a first set of k-space data. The first set of k-space data may be obtained by filling reference MR signals into the k-space along a reference trajectory. The k-space may be in a Cartesian coordinate system. In some embodiments, the reference MRI signals may be the same as the target MRI signals. In some embodiments, the reference MRI signals may be different from the target MRI signals. For example, the reference MRI signals and the target MRI signals may be MRI scan data acquired by the MRI device (e.g., the MRI device 110) in different time periods during an MRI scan of the subject (e.g., a patient). The reference trajectory may include a Cartesian trajectory. The processing device 120 may generate a second image based on a second set of k-space data. The second set of k-space data may be obtained by filling the reference MR signals into the k-space along the corkscrew trajectory. In some embodiments, the processing device 120 may generate the first image and the second image based on one or more image reconstruction techniques. Exemplary reconstruction techniques may include Fourier reconstruction, inverse Fourier reconstruction, constrained image reconstruction, regularized image reconstruction in parallel MRI, compressed-sensing (CS)-parallel imaging (PI) reconstruction, or the like, or any combination thereof. Exemplary CS-PI reconstruction techniques may include sparse sensitivity encoding (SENSE), l1-iterative self-consistent parallel imaging reconstruction (SPIRIT), CS-SENSE, CS-generalized autocalibrating partially parallel acquisitions (GRAPPA), or the like, or any combination thereof.

Further, the processing device 120 may determine the point spread function based on the first image and the second image. In some embodiments, each pixel (or voxel) in an MRI image (e.g., the first image, the second image) may include phase information and magnitude information reflecting an interaction between the subject and magnetic fields generated by the MRI device. The processing device 120 may determine the point spread function based on phase information associated with the first image and the second image. In some embodiments, the processing device 120 may determine a phase difference between the first image and the second image as the point spread function. For example, the processing device 120 may determine a first phase matrix of the first image based on values of pixels (or voxels) in the first image. A value in the first phase matrix of the first image may be a phase value of a corresponding pixel (or voxel) in the first image. The processing device 120 may determine a second phase matrix of the second image based on values of pixels (or voxels) in the second image. A value in the second phase matrix of the second image may be a phase value of a corresponding pixel (or voxel) in the second image. The processing device 120 may determine a phase difference matrix between the first phase matrix of the first image and the second phase matrix of the second image as the point spread function.

In 640, the processing device 120 (e.g., the determination module 520) may generate a target image based on an objective function. For example, the target image may be determined by solving the objective function iteratively. The objective function may be determined based on an operator, the plurality of target sets of k-space data, the plurality of coil sensitivities, and the point spread function. The operator may represent a mapping relationship between the target image and the plurality of target sets of k-space data.

The objective function may be used to determine the target image. The target image may be set as an independent variable in the objective function. In some embodiments, the processing device 120 may determine the objective function based on the operator and an aliased image. As used herein, an aliased image refers to an image directly transformed into image domain based on undersampled k-space data (e.g., the target set of k-space data). For example, the aliased image may be obtained by performing an inverse Fourier transform on the undersam pled k-space data (e.g., the target set of k-space data). In some embodiments, the aliased image may include an aliasing artifact (i.e., aliasing pixels). As used herein, a target image (also referred to as an unaliased image) refers to an image with reduced aliasing or without aliasing.

For example, the processing device 120 may determine the operator based on the plurality of coil sensitivities, the point spread function, and the mask. The processing device 120 may determine the aliased image based on the plurality of target sets of k-space data, the plurality of coil sensitivities, and the point spread function. The processing device 120 may determine the objective function based on the operator and the aliased image. Further, the processing device 120 may determine the target image based on the objective function. More descriptions of the determination of the aliased image, the objective function and the target image may be found elsewhere in the present disclosure (e.g., FIG. 7 and descriptions thereof).

In some embodiments, the processing device 120 may obtain a plurality of target sets of k-space data by filling target MR signals acquired by a plurality of coils of an MRI device into k-space along a corkscrew trajectory as described in connection with operation 610. The processing device 120 may determine an aliased image related to the plurality of coils based on the plurality of target sets of k-space data. For example, the processing device 120 may determine a plurality of intermediate images corresponding to the plurality of coils based on the plurality of target sets of k-space data, a plurality of coil sensitivities, and a point spread function corresponding to the corkscrew trajectory. The processing device 120 may generate the aliased image based on the plurality of intermediate images corresponding to the plurality of coils. The processing device 120 may determine a target image based on the aliased image and a mapping relationship (i.e., the operator) between the target image and the aliased image. In some embodiments, the processing device 120 may determine the mapping relationship (i.e., the operator) based on a plurality of coil sensitivities, a point spread function corresponding to the corkscrew trajectory, and a mask corresponding to the corkscrew trajectory. In some embodiments, the processing device 120 may determine an objective function based on the aliased image and the mapping relationship. The processing device 120 may generate the target image by solving the objective function iteratively. More descriptions of the determination of the aliased image, the objective function and the target image may be found elsewhere in the present disclosure (e.g., FIG. 7 and descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 7:
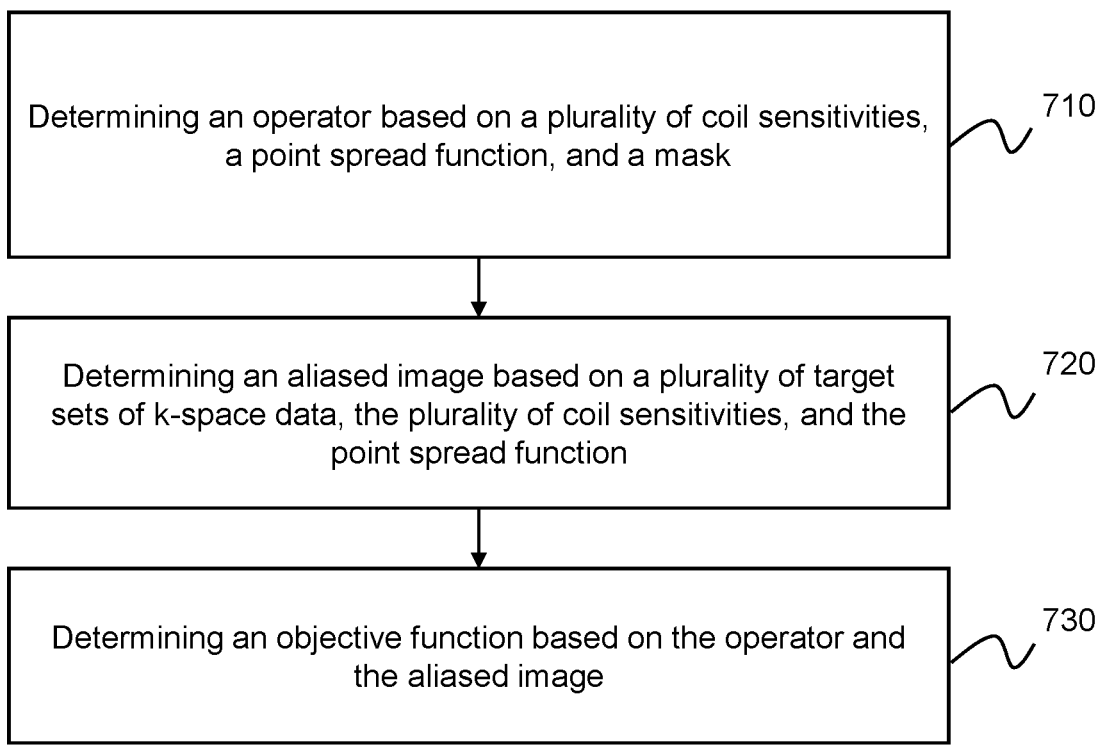
FIG. 7 is a flowchart illustrating an exemplary process for determining an objective function according to some embodiments of the present disclosure.

FIG. 7 is a flowchart illustrating an exemplary process for determining an objective function according to some embodiments of the present disclosure. In some embodiments, the process 700 may be implemented in the MRI system 100 illustrated in FIG. 1. For example, the process 700 may be stored in the storage device 130 and/or the storage (e.g., the storage 320, the storage 490) as a form of instructions, and invoked and/or executed by the processing device 120 (e.g., the processor 310 of the computing device 300 as illustrated in FIG. 3, the CPU 440 of the mobile device 400 as illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, at least a part of operation 640 illustrated in FIG. 6 may be performed according to the process 700.

In 710, the processing device 120 (e.g., the determination module 520) may determine an operator based on a plurality of coil sensitivities, a point spread function, and a mask.

The operator may describe an undersampling process of k-space data (e.g., fully sampled k-space data) corresponding to a target image to generate undersampled k-space data (e.g., the target set of k-space data) for reconstructing an aliased image. For example, the operator may describe a mapping relationship between the target image and the undersampled k-space data (e.g., the target set of k-space data). As another example, the operator may describe a mapping relationship between the target image and the aliased image.

In some embodiments, for each coil of the plurality of coils of an MRI device, the processing device 120 may generate a first candidate image related to the coil based on a coil sensitivity of the coil and the target image. As used herein, "an image related to a coil" refers to an image generated based on MRI signals (e.g., a plurality of echo signals) detected by the coil. For example, the processing device 120 may generate the first candidate image related to the coil by multiplying a coil sensitivity of the coil and the target image.

The processing device 120 may determine a first candidate set of k-space data based on the first candidate image, the point spread function, and the mask. The first candidate set of k-space data may correspond to the undersampled k-space data (e.g., the target set of k-space data). Taking the target image and the first candidate image being 3D images as an example, the processing device 120 may generate a first processed candidate image by performing a first Fourier transform on the first candidate image along a first direction (e.g., the Kx direction) of the k-space. The processing device 120 may generate a second processed candidate image by multiplying the point spread function and the first processed candidate image. Since the point spread function describes the effect of the wave gradients (i.e., each readout line in the target image is convolved with the point spread function to yield the acquired aliased image), by multiplying the point spread function and the first processed candidate image, the effect of the wave gradients is embodied. The processing device 120 may generate a third processed candidate image by performing a second Fourier transform on the second processed candidate image along a second direction (e.g., the Ky direction) of the k-space. The processing device 120 may generate a second candidate set of k-space data by performing a third Fourier transform on the third processed candidate image along a third direction (e.g., the Kz direction) of the k-space. The second candidate set of k-space data may correspond to the fully sampled k-space data corresponding to the target image. The processing device 120 may generate the first candidate set of k-space data based on the second candidate set of k-space data and the mask. For example, the processing device 120 may generate the first candidate set of k-space data by multiplying the second candidate set of k-space data and the mask. In the present disclosure, the first processed candidate image, the second processed candidate, and/or the image third processed candidate image may also be referred to as temporary data or intermediate results.

Then, processing device 120 may transform the first candidate set of k-space data from the frequency domain to the image domain. In some embodiments, the processing device 120 may generate a second candidate image related to the coil by processing the first candidate set of k-space data based on the point spread function and the coil sensitivity of the coil. For example, the processing device 120 may generate a first processed candidate set of k-space data by performing a first inverse Fourier transform on the first candidate set of k-space data along the third direction (e.g., the Kz direction) of the k-space. The processing device 120 may generate a second processed candidate set of k-space data by performing a second inverse Fourier transform on the first processed candidate set of k-space data along the second direction (e.g., the Ky direction) of the k-space. The processing device 120 may generate a third processed candidate set of k-space data by multiplying the second processed candidate set of k-space data and a conjugation of the point spread function. In some embodiments, a conjugation of the point spread function may be a conjugation matrix of the point spread function. For example, a conjugation matrix of a specific matrix (e.g., the point spread function) may be obtained by taking the complex conjugate of each element of the specific matrix (e.g., the point spread function). By multiplying the second processed candidate set of k-space data and a conjugation of the point spread function, the effect of the wave gradients may be eliminated. The processing device 120 may generate a third candidate image by performing a third inverse Fourier transform on the third processed candidate set of k-space data along the first direction (e.g., the Kx direction) of the k-space. The processing device 120 may generate the second candidate image by multiplying the third candidate image and a conjugation of the coil sensitivity of the coil. In some embodiments, a conjugation of the coil sensitivity may be a conjugation matrix of the coil sensitivity. By multiplying the third candidate image and the conjugation of the coil sensitivity of the coil, the effect of coil sensitivities of the plurality of coils may be eliminated. In the present disclosure, the first processed candidate set of k-space data, the second processed candidate set of k-space data, and/or the third processed candidate set of k-space data may also be referred to as temporary data or intermediate results.

The processing device 120 may determine the operator based on a plurality of second candidate images related to the plurality of coils. In some embodiments, the processing device 120 may determine the operator by combining the plurality of second candidate images related to the plurality of coils. For example, if the plurality of second candidate images are presented as A1, A2, A3, . . . , and An, the operator may be determined as (A1+A2+A3, . . . , +An). For illustration purposes, memory spaces "Buffer" and "Res" may be established. The "Buffer" and the "Res" may be used to store an initial, intermediate, or final result of the operator. The size of "Buffer" and the size of "Res" may be the same as the size of the target image. Elements in the "Buffer" and the "Res" may be assigned initial values, e.g., zero. Different elements in the "Buffer" may be assigned a same initial value or different initial values. For example, elements in "Buffer" may be assigned any suitable values. Different elements in the "Res" may be assigned a same initial value. For example, all elements in the "Res" may be assigned zero. The operator may be determined according to a computer code set forth below:

```
Loop j = 1: Nc
    Buffer = Im * S_j;
    Buffer = Fx(Buffer);
    Buffer = Buffer * Psfs;
    Buffer = Fy(Buffer);
    Buffer = Fz(Buffer);
    Buffer = Buffer * mask;
    Buffer = iFz(Buffer);
    Buffer = iFy(Buffer);
```

```
Buffer = Buffer * conj(Psfs);
Buffer = iFx(Buffer);
Buffer = Buffer * conj(S_j);
Res = Res + Buffer;
end
```

When the iteration or loop is completed, the "Buffer" may be reset (e.g., by assigning the elements of the "Buffer" an initial value of zero, and return the "Res" as a result, where Res refers to the operator; Nc refers to a number (or count) of coils; Im refers to a target image; $S_j$ refers to a coil sensitivity of a jth coil; Fx refers to a Fourier transform operation in a Kx direction; Fy refers to a Fourier transform operation in a Ky direction; Fz refers to a Fourier transform operation in a Kz direction; iFx refers to a first inverse Fourier transform operation in the Kx direction; iFy refers to a second inverse Fourier transform operation in the Ky direction; iFz refers to a third inverse Fourier transform operation in the Kz direction; Psfs refers to a point spread function; conj refers to a conjugation operation; and the symbol "*" refers to a point-to-point multiplication of matrixes or arrays.

In 720, the processing device 120 (e.g., the determination module 520) may determine an aliased image based on a plurality of target sets of k-space data, the plurality of coil sensitivities, and the point spread function.

Taking the target set of k-space data being 3D k-space data as an example, for each target set of k-space data of the plurality of target sets of k-space data, the processing device 120 may generate a first processed target set of k-space data by performing a first inverse Fourier transform on the target set of k-space data along the third direction (e.g., the Kz direction) of the k-space. The processing device 120 may generate a second processed target set of k-space data by performing a second inverse Fourier transform on the first processed target set of k-space data along the second direction (e.g., the Ky direction) of the k-space. The processing device 120 may generate a third processed target set of k-space data by multiplying the second processed target set of k-space data and a conjugation of the point spread function. The processing device 120 may generate a first intermediate image related to a coil corresponding to the target set of k-space data by performing a third inverse Fourier transform on the third processed target set of k-space data along the first direction (e.g., the Kx direction) of the k-space. The processing device 120 may generate a second intermediate image related to the coil based on a coil sensitivity of the coil and the first intermediate image. For example, the processing device 120 may generate the second intermediate image related to the coil by multiplying the first intermediate image and a conjugation of the coil sensitivity of the coil. In the present disclosure, the first processed target set of k-space data, the second processed target set of k-space data, and/or the third processed target set of k-space data may also be referred to as temporary data or intermediate results.

The processing device 120 may generate the aliased image based on a plurality of second intermediate images related to the plurality of coils corresponding to the plurality of target sets of k-space data. In some embodiments, the processing device 120 may generate the aliased image by combining the plurality of second intermediate images related to the plurality of coils corresponding to the plurality of target sets of k-space data. Merely by way of example, the processing device 120 may determine an average image of the plurality of second intermediate images as the aliased image. The processing device 120 may determine the average image of the plurality of second intermediate images based on a voxel value of each voxel of a plurality of voxels in each of the plurality of second intermediate images. For example, the processing device 120 may determine an average voxel value of a plurality of corresponding voxels in the plurality of second intermediate images. As used herein, voxels in a plurality of images (e.g., the plurality of second intermediate images) are considered corresponding when the voxels correspond to a same physical location of the subject or space where in the subject is located. The processing device 120 may determine the average image based on a plurality of average voxel values.

For illustration purposes, memory spaces "Buffer" and "b" may be established. The "Buffer" and the "b" may be used to store an initial, intermediate, or final result of the aliased image. The size of "Buffer" and the size of "b" may be the same as the size of the target image. Elements in the "Buffer" and the "b" may be assigned initial values, e.g., zero. Different elements in the "Buffer" may be assigned a same initial value or different initial values. For example, elements in "Buffer" may be assigned any suitable values. Different elements in the "b" may be assigned a same initial value. For example, all elements in the "b" may be assigned zero. The aliased image may be determined according to a computer code set forth below:

```
Loop j = 1: Nc
    Buffer = iFy (iFz(y_j));
    Buffer = Buffer * conj(Psfs);
    Buffer = iFx(Buffer);
    Buffer = Buffer * conj(S_j);
    b = b + Buffer;
end.
```

When the iteration or loop is completed, the "Buffer" may be reset (e.g., by assigning the elements of the "Buffer" an initial value of zero, and return the "b" as a result, where b refers to the aliased image; Nc refers to a number (or count) of coils; $S_j$ refers to a coil sensitivity of a jth coil; iFx refers to a first inverse Fourier transform operation in the Kx direction; iFy refers to a second inverse Fourier transform operation in the Ky direction; iFz refers to a third inverse Fourier transform operation in the Kz direction; Psfs refers to a point spread function; conj refers to a conjugation operation; and the symbol "*" refers to a point-to-point multiplication of matrixes or arrays.

According to some embodiments of the present disclosure, the operator and the aliased image may be determined based on algorithms illustrated above, the calculation speed of the objective function may be improved, and the memory space may be saved.

In 730, the processing device 120 (e.g., the determination module 520) may determine an objective function based on the operator and the aliased image.

The target image may be set as an independent variable in the objective function. For example, the processing device 120 may determine the objective function based on the operator and the aliased image according to Equation (4):

$$optA(x)=b, \quad (4)$$

where optA(x) refers to an operator; b refers to an aliased image; and x refers to a target image.

The processing device 120 may determine the target image based on the objective function. In some embodiments, the processing device 120 may determine the target image based on the objective function according to an iterative algorithm. For example, the processing device 120 may determine the target image based on the objective function according to a conjugate gradient algorithm.

For illustration purposes, memory spaces "$r_0$" and "$p_0$" may be established. The size of "$r_0$" and the size of "$p_0$" may be the same as the size of the target image. Elements in the "$r_0$" and the "$p_0$" may be assigned initial values, e.g., zero. The target image may be determined according to a computer code set forth below:

$r_0 = b - optA(x)$ $p_0 = r_0$ $k = 0$ repeat:

$$\alpha_k = \frac{r_k^T r_k}{p_k^T optA(p_k)}$$

$$x_{k+1} = x_k + \alpha_k p_k$$

$$r_{k+1} = r_k - \alpha_k optA(p_k)$$

If $r_{k+1}$ is sufficiently small, then exit loop, and $$\beta_k = \frac{r_{k+1}^T r_{k+1}}{r_k^T r_k}$$

$$p_{k+1} = r_{k+1} + \beta_k p_k$$

$$k = k + 1$$

end.

When the iteration is completed, the "$r_0$" and the "$p_0$" may be reset (e.g., by assigning the elements of the "$r_0$" and the "$p_0$" an initial value of zero, and return the "$x_{k+1}$" as a result, where $x_{k+1}$ refers to a target image; $p_0$ and $r_0$ refers to the negative of the gradient of the operator (i.e., optA) at $x=x_0$; $\alpha_k$ refers to a step size; $r_k$ refers to a residual at the k-th step, which means the negative gradient of the operator (i.e., optA) at $x_k$; $p_k$ refers to a search direction in the k-th step; $\beta_k$ refers to a step size of $p_k$; and k refers to a number (or count) of iterations.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the target image may be a 2D image and the target set of k-space data may be 2D k-space data. The processing device 120 may determine the objective function according to process 700 by deleting operations performed along the third direction (e.g., the Kz direction) of the k-space.

In order to better understand the establishment of the objective function, the following is an example to illustrate the idea of establishing the objective function. Usually when an equation Y=FSX in MRI is solved, wherein Y refers to k-space data, F refers to a Fourier transform operation, S refers to a point spread function, and X refers to a target image, the left side and the right side of the equation may be multiplied by a transpose of FS (i.e., S'F') at the same time, the equation may become S'F'Y=S'F'FSX. Accordingly, the operator determined in operation 710 may be considered as S'F'FS(X) in the equation S'F'Y=S'F'FSX, and the aliased image determined in operation 720 may be considered as S'F'Y in the equation S'F'Y=S'F'FSX.

Figure 8A:
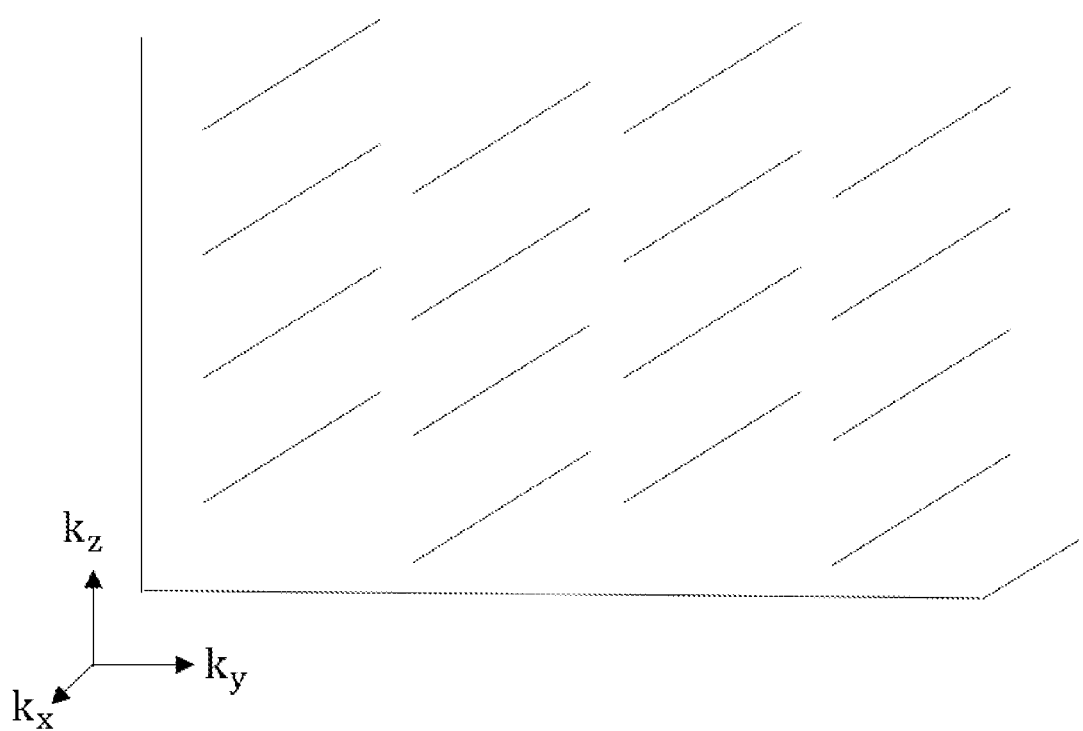
FIG. 8A is a schematic diagram illustrating an exemplary Cartesian sampling pattern according to some embodiments of the present disclosure.
Figure 8B:
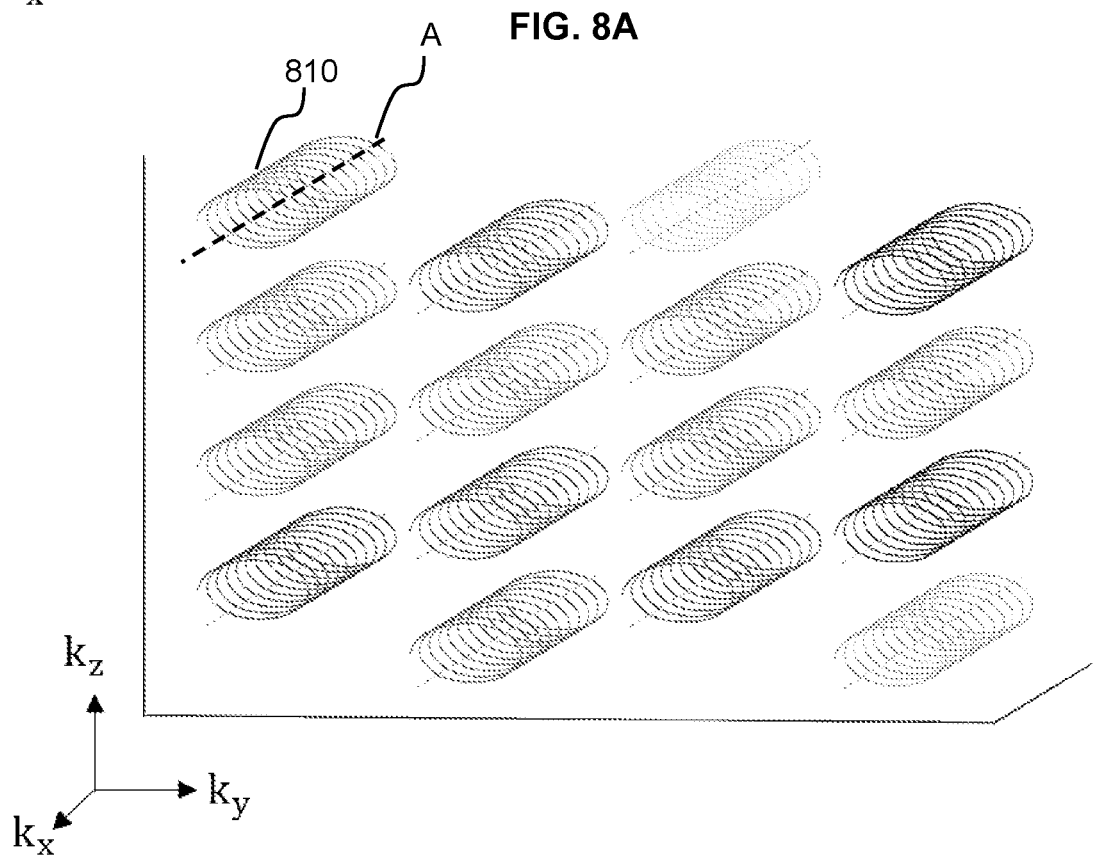
FIG. 8B is a schematic diagram illustrating an exemplary corkscrew sampling pattern according to some embodiments of the present disclosure.

FIG. 8A is a schematic diagram illustrating an exemplary Cartesian sampling pattern according to some embodiments of the present disclosure. FIG. 8B is a schematic diagram illustrating an exemplary corkscrew sampling pattern according to some embodiments of the present disclosure.

As illustrated in FIGS. 8A and 8B, Kx represents a frequency encoding direction, Ky represents a phase encoding direction, and Kz represents a slice selection direction. As illustrated in FIG. 8A, the Cartesian sampling pattern includes a plurality of straight trajectories along the Kx direction. As illustrated FIG. 8B, the corkscrew sampling pattern includes a plurality of corkscrew trajectories along the Kx direction. A central axis of each corkscrew trajectory (e.g., a central axis A of a corkscrew trajectory 810) is parallel to the Kx direction.

In some embodiments, if the corkscrew sampling pattern is a uniform corkscrew trajectory, the plurality of corkscrew trajectories may be uniformly distributed in the k-space. For example, a distance between central axes of adjacent corkscrew trajectories may be the same. In some embodiments, if the corkscrew sampling pattern is a random corkscrew trajectory, the plurality of corkscrew trajectories may be randomly distributed in the k-space. For example, a distance between central axes of adjacent corkscrew trajectories may be different. In some embodiments, if the corkscrew sampling pattern is a variable density corkscrew trajectory, the plurality of corkscrew trajectories may be distributed in the k-space with variable densities. For example, in the Ky direction and/or the Kz direction, a sampling density may change over the k-space location. The sampling density in a central k-space region may be relatively high, and the sampling density in an outer k-space region may be relatively low, as illustrated in FIG. 9A.

FIG. 9A is a schematic diagram illustrating an exemplary variable density sampling pattern according to some embodiments of the present disclosure. FIG. 9B is a schematic diagram illustrating an exemplary CAIPIRINHA sampling pattern according to some embodiments of the present disclosure.

As illustrated in FIGS. 9A and 9B, Ky represents a phase encoding direction, Kz represents a slice selection direction, and a white dot refers to a sampled data point in k-space. As illustrated in FIG. 9A, for the variable density sampling pattern, in both the Ky direction and the Kz direction, a sampling density changes over the k-space location. As illustrated, the sampling density in a central k-space region may be relatively high, and the sampling density in an outer k-space region may be relatively low. For example, the central k-space region may be fully sampled, and the outer k-space region may be undersampled. In a Kx direction (not shown in FIG. 9A), the k-space may be fully sampled or undersampled. As illustrated in FIG. 9B, for the CAIPIRINHA sampling pattern, in both the Ky direction and the Kz direction, the k-space is undersampled. In the Kx direction (not shown in FIG. 9B), the k-space may be fully sampled or undersampled.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A method for magnetic resonance imaging (MRI) implemented on a computing device having at least one processor and at least one storage device, the method comprising:

obtaining a plurality of target sets of k-space data by filling target MR signals acquired by a plurality of coils of an MRI device into k-space along a corkscrew trajectory;

obtaining a coil sensitivity of each of the plurality of coils;

obtaining a point spread function corresponding to the corkscrew trajectory; and generating a target image based on an objective function, wherein the objective function is determined based on an operator, the plurality of target sets of k-space data, the plurality of coil sensitivities, and the point spread function, and the operator represents a mapping relationship between the target image and the plurality of target sets of k-space data, wherein the obtaining point spread function corresponding to the corkscrew trajectory comprises:

generating a first image based on a first set of k-space data, wherein the first set of k-space data is obtained by filling reference MR signals into the k-space along a reference trajectory;

generating a second image based on a second set of k-space data, wherein the second set of k-space data is obtained by filling the reference MR signals into the k-space along the corkscrew trajectory; and determining the point spread function based on the first image and the second image.

2. The method of claim 1, wherein the plurality of target sets of k-space data are obtained by filling the target MR signals into the k-space with variable densities.

3. The method of claim 1, wherein the point spread function is determined based on a phase difference matrix between the first image and the second image.

4. The method of claim 1, wherein each target set of k-space data corresponds to the target MR signals acquired by a coil of the plurality of coils of the MRI device, and the obtaining a plurality of target sets of k-space data comprises:

for the each target set of k-space data of the plurality of target sets of k-space data,
obtaining the target MR signals acquired by the coil of the plurality of coils of the MRI device;
obtaining a mask; and
obtaining the target set of k-space data based on the target MR signals and the mask.

5. The method of claim 4, wherein the generating a target image based on an objective function comprises:

setting the target image as an independent variable in the objective function.

6. The method of claim 5, wherein the objective function is determined based on the operator, the plurality of target sets of k-space data, the plurality of coil sensitivities, and the point spread function by a process comprising:

determining the operator based on the plurality of coil sensitivities, the point spread function, and the mask;
determining an aliased image based on the plurality of target sets of k-space data, the plurality of coil sensitivities, and the point spread function; and
determining the objective function based on the operator and the aliased image.

7. The method of claim 6, wherein the determining the operator based on the plurality of coil sensitivities, the point spread function comprises:

for each coil of the plurality of coils of the MRI device,
generating a first candidate image related to the coil based on a coil sensitivity of the coil and the target image;
determining a first candidate set of k-space data based on the first candidate image, the point spread function, and the mask;
generating a second candidate image related to the coil by processing the first candidate set of k-space data based on the point spread function and the coil sensitivity of the coil; and
determining the operator based on a plurality of second candidate images related to the plurality of coils.

8. The method of claim 7, wherein the k-space is three-dimensional, the first candidate image is a three-dimensional image, and the determining a first candidate set of k-space data based on the first candidate image, the point spread function, and the mask comprises:

generating a first processed candidate image by performing a first Fourier transform on the first candidate image along a first direction of the k-space;
generating a second processed candidate image by multiplying the point spread function and the first processed candidate image;
generating a third processed candidate image by performing a second Fourier transform on the second processed candidate image along a second direction of the k-space;
generating a second candidate set of k-space data by performing a third Fourier transform on the third processed candidate image along a third direction of the k-space; and
generating the first candidate set of k-space data based on the second candidate set of k-space data and the mask, wherein the first direction, the second direction, and the third direction are orthogonal to each other.

9. The method of claim 8, wherein the generating a second candidate image related to the coil by processing the first candidate set of k-space data based on the point spread function and the coil sensitivity of the coil comprises:

generating a first processed candidate set of k-space data by performing a first inverse Fourier transform on the first candidate set of k-space data along the third direction of the k-space;
generating a second processed candidate set of k-space data by performing a second inverse Fourier transform on the first processed candidate set of k-space data along the second direction of the k-space;
generating a third processed candidate set of k-space data by multiplying the second processed candidate set of k-space data and a conjugation of the point spread function;
generating a third candidate image by performing a third inverse Fourier transform on the third processed candidate set of k-space data along the first direction of the k-space; and
generating the second candidate image by multiplying the third candidate image and a conjugation of the coil sensitivity of the coil.

10. The method of claim 6, wherein the k-space is three-dimensional, the target set of k-space data is three-dimensional, and the determining the aliased image based on the plurality of target sets of k-space data, the plurality of coil sensitivities, and the point spread function comprises:

for the each target set of k-space data of the plurality of target sets of k-space data,
generating a first processed target set of k-space data by performing a first inverse Fourier transform on the target set of k-space data along a third direction of the k-space;
generating a second processed target set of k-space data by performing a second inverse Fourier transform on the first processed target set of k-space data along a second direction of the k-space;
generating a third processed target set of k-space data by multiplying the second processed target set of k-space data and a conjugation of the point spread function;
generating a first intermediate image related to a coil corresponding to the target set of k-space data by performing a third inverse Fourier transform on the third processed target set of k-space data along a first direction of the k-space; and
generating a second intermediate image related to the coil based on a coil sensitivity of the coil and the first intermediate image; and
generating the aliased image based on a plurality of second intermediate images related to the plurality of coils.

11. The method of claim 1, wherein the determining the target image based on the objective function comprises:
determining the target image based on the objective function according to a conjugate gradient algorithm.

12. The method of claim 1, wherein the obtaining a plurality of target sets of k-space data by filling target MR signals acquired by a plurality of coils of an MRI device into k-space along a corkscrew trajectory comprises:
obtaining the plurality of target sets of k-space data by filling the target MR signals acquired by the plurality of coils of the MRI device into the k-space along a random corkscrew trajectory.

13. A system for magnetic resonance imaging (MRI), comprising:
at least one storage device storing a set of instructions; and
at least one processor in communication with the at least one storage device, when executing the stored set of instructions, the at least one processor causes the system to perform operations including:
obtaining a plurality of target sets of k-space data by filling target MR signals acquired by a plurality of coils of an MRI device into k-space along a corkscrew trajectory;
obtaining a coil sensitivity of each of the plurality of coils;
obtaining a point spread function corresponding to the corkscrew trajectory; and
generating a target image based on an objective function, wherein
the objective function is determined based on an operator, the plurality of target sets of k-space data, the plurality of coil sensitivities, and the point spread function, and
the operator represents a mapping relationship between the target image and the plurality of target sets of k-space data, wherein the obtaining the point spread function corresponding to the corkscrew trajectory comprises:
generating a first image based on a first set of k-space data, wherein the first set of k-space data is obtained by filling reference MR signals into the k-space along a reference trajectory;
generating a second image based on a second set of k-space data, wherein the second set of k-space data is obtained by filling the reference MR signals into the k-space along the corkscrew trajectory; and
determining the point spread function based on the first image and the second image.

14. The system of claim 13, wherein the plurality of target sets of k-space data are obtained by filling the target MR signals into the k-space with variable densities.

15. The system of claim 13, wherein the point spread function is determined based on a phase difference matrix between the first image and the second image.

16. The system of claim 13, wherein each target set of k-space data corresponds to the target MR signals acquired by a coil of the plurality of coils of the MRI device, and the obtaining a plurality of target sets of k-space data comprises:
for the each target set of k-space data of the plurality of target sets of k-space data,
obtaining the target MR signals acquired by the coil of the plurality of coils of the MRI device;
obtaining a mask; and
obtaining the target set of k-space data based on the target MR signals and the mask.

17. A method for magnetic resonance imaging (MRI) implemented on a computing device having at least one processor and at least one storage device, the method comprising:
obtaining a plurality of target sets of k-space data by filling target MR signals acquired by a plurality of coils of an MRI device into k-space along a corkscrew trajectory;
determining an aliased image related to the plurality of coils based on the plurality of target sets of k-space data and a point spread function; and
determining a target image based on the aliased image and a mapping relationship between the target image and the aliased image, wherein the point spread function is obtained by:
generating a first image based on a first set of k-space data, wherein the first set of k-space data is obtained by filling reference MR signals into the k-space along a reference trajectory;
generating a second image based on a second set of k-space data, wherein the second set of k-space data is obtained by filling the reference MR signals into the k-space along the corkscrew trajectory; and
determining the point spread function based on the first image and the second image.

18. The method of claim 17, wherein the determining a target image based on the aliased image and a mapping relationship between the target image and the aliased image comprises:
determining an objective function based on the aliased image and the mapping relationship; and
generating the target image by solving the objective function iteratively.

19. The method of claim 17, further comprising:
determining the mapping relationship based on a plurality of coil sensitivities, a point spread function corresponding to the corkscrew trajectory, and a mask corresponding to the corkscrew trajectory.

20. The method of claim 17, wherein the determining an aliased image related to the plurality of coils based on the plurality of target sets of k-space data comprises:
determining a plurality of intermediate images corresponding to the plurality of coils based on the plurality of target sets of k-space data, a plurality of coil sensitivities, and the point spread function corresponding to the corkscrew trajectory; and
generating the aliased image based on the plurality of intermediate images corresponding to the plurality of coils.

* * * * *